(12) United States Patent
Dunne et al.

(10) Patent No.: US 10,124,129 B2
(45) Date of Patent: Nov. 13, 2018

(54) DISPENSING DEVICE, STORAGE DEVICE AND METHOD FOR DISPENSING A FORMULATION

(75) Inventors: Stephen T. Dunne, Stowmarket (GB); Achim Moser, Chemnitz (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 1032 days.

(21) Appl. No.: 12/808,686

(22) PCT Filed: Dec. 24, 2008

(86) PCT No.: PCT/EP2008/011112
§ 371 (c)(1),
(2), (4) Date: Jul. 30, 2010

(87) PCT Pub. No.: WO2009/083244
PCT Pub. Date: Jul. 9, 2009

(65) Prior Publication Data
US 2011/0277753 A1 Nov. 17, 2011

(30) Foreign Application Priority Data
Jan. 2, 2008 (EP) .................... 08000010

(51) Int. Cl.
*A61M 11/00* (2006.01)
*A61M 15/00* (2006.01)
(52) U.S. Cl.
CPC ...... *A61M 15/0045* (2013.01); *A61M 11/001* (2014.02); *A61M 15/0031* (2014.02);
(Continued)

(58) Field of Classification Search
CPC .............. A61M 15/00; A61M 15/0001; A61M 15/0028; A61M 15/003; A61M 15/0031;
(Continued)

(56) References Cited

U.S. PATENT DOCUMENTS

| 1,828,864 A | 10/1931 | Hopkins |
| 2,015,970 A | 10/1935 | Schoene |

(Continued)

FOREIGN PATENT DOCUMENTS

| AU | 2005201364 A1 | 7/2006 |
| CA | 1094549 A | 1/1981 |

(Continued)

OTHER PUBLICATIONS

International Search Report for PCT/EP2008/011112 dated Sep. 3, 2009.

(Continued)

*Primary Examiner* — (Jackie) Tan-Uyen T Ho
*Assistant Examiner* — Joseph D Boecker
(74) *Attorney, Agent, or Firm* — Matthew B. Dernier, Esq.

(57) ABSTRACT

The invention relates to a dispensing device, a storage device and a method for dispensing a medical formulation. Multiple doses of the formulation are stored in a carrier having multiple storage members, each storage member containing a single dose. Each storage member comprises one duct or nozzle for dispensing the respective dose. The dispensing direction of the ducts or nozzles is directed in a lengthwise or indexing direction of the carrier. The storage device of the carrier is a peelable blister strip, wherein the ducts or nozzles can be opened one after the other by peeling the blister strip.

19 Claims, 3 Drawing Sheets

(52) U.S. Cl.
CPC .... *A61M 15/0043* (2014.02); *A61M 15/0051* (2014.02); *A61M 15/0061* (2014.02); *A61M 2202/064* (2013.01); *A61M 2205/07* (2013.01); *A61M 2205/071* (2013.01)

(58) Field of Classification Search
CPC .......... A61M 15/0043; A61M 15/0045; A61M 15/0046; A61M 15/0048; A61M 15/0051; A61M 15/0061; A61M 15/0063; A61M 11/00; A61M 11/001; A61M 2202/064
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,348,726 A | 10/1967 | LaCross |
| 3,354,883 A | 11/1967 | Southerland |
| 3,425,591 A | 2/1969 | Pugh |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,606,106 A | 9/1971 | Yuhas |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,684,124 A | 8/1972 | Song |
| 3,802,604 A | 4/1974 | Morane et al. |
| 3,817,416 A | 6/1974 | Costa |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,120,995 A | 10/1978 | Phipps et al. |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,434,908 A | 3/1984 | French |
| 4,456,016 A | 6/1984 | Nowacki et al. |
| 4,463,867 A | 8/1984 | Nagel |
| 4,467,965 A | 8/1984 | Skinner |
| 4,474,302 A | 10/1984 | Goldberg et al. |
| 4,476,116 A | 10/1984 | Anik |
| 4,515,586 A | 5/1985 | Mendenhall et al. |
| 4,516,967 A | 5/1985 | Kopfer |
| 4,524,888 A | 6/1985 | Tada |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,441 E | 11/1990 | Lemer |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A * | 5/1993 | Cocozza et al. ......... 128/203.21 |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A * | 4/1996 | Lloyd et al. ............. 128/200.14 |
| 5,518,147 A | 5/1996 | Peterson et al. |
| 5,533,994 A | 7/1996 | Meyer |
| 5,541,569 A | 7/1996 | Jang |
| 5,544,646 A * | 8/1996 | Lloyd et al. ............. 128/200.14 |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A | 12/1996 | Salter et al. |

(56) References Cited

U.S. PATENT DOCUMENTS

| | | |
|---|---|---|
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A * | 1/1998 | Lloyd et al. ............ 128/200.14 |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A * | 11/1998 | Rubsamen et al. ...... 128/203.21 |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A * | 8/1999 | Lloyd et al. ............ 128/200.22 |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A | 3/2000 | Faithfull et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,446,054 B1 | 9/2002 | Mayorga |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 * | 9/2004 | Davies et al. ............ 128/203.15 |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 * | 5/2005 | Crowder et al. ......... 128/203.15 |
| 6,890,517 B2 | 5/2005 | Drechsel et al. |
| 6,915,901 B2 | 7/2005 | Feinberg et al. |
| 6,929,004 B1 * | 8/2005 | Bonney et al. .......... 128/203.15 |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,152,760 B1 | 12/2006 | Peabody |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 * | 7/2009 | Mori .................... B60J 7/146 296/107.17 |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |

(56) References Cited

U.S. PATENT DOCUMENTS

| | | |
|---|---|---|
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,104,643 B2 | 1/2012 | Pruvot |
| 8,167,171 B2 | 5/2012 | Moretti |
| 8,298,622 B2 | 10/2012 | Nakayama et al. |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,944,292 B2 | 2/2015 | Moreau |
| 8,950,393 B2 | 2/2015 | Holakovsky et al. |
| 8,960,188 B2 | 2/2015 | Bach et al. |
| 8,997,735 B2 | 4/2015 | Zierenberg et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 9,744,313 B2 | 8/2017 | Besseler et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0005195 A1 | 1/2002 | Shick et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1* | 7/2002 | Connelly .......... A61M 15/0028 128/203.15 |
| 2002/0111363 A1 | 8/2002 | Drechsel et al. |
| 2002/0129812 A1 | 9/2002 | Litherland et al. |
| 2002/0130195 A1 | 9/2002 | Jaeger et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0066815 A1 | 4/2003 | Lucas |
| 2003/0080210 A1 | 5/2003 | Jaeger et al. |
| 2003/0085254 A1 | 5/2003 | Katooka et al. |
| 2003/0098023 A1 | 5/2003 | Drachmann et al. |
| 2003/0106827 A1* | 6/2003 | Cheu et al. .................. 206/531 |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1 | 10/2003 | Haveri |
| 2003/0209238 A1 | 11/2003 | Peters et al. |
| 2003/0226907 A1 | 12/2003 | Geser et al. |
| 2003/0234203 A1* | 12/2003 | Urban .................. B65D 75/327 206/530 |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0164186 A1 | 8/2004 | Kladders et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028812 A1 | 2/2005 | Djupesland |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1* | 12/2005 | Bonney et al. .......... 128/203.15 |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239886 A1 | 10/2006 | Nakayama et al. |
| 2006/0239930 A1 | 10/2006 | Lamche et al. |
| 2006/0254579 A1 | 11/2006 | Grychowski et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1* | 7/2007 | Rohrschneider .. A61M 15/0045 128/200.19 |
| 2007/0181526 A1 | 8/2007 | Frishman |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0264437 A1 | 11/2007 | Zimmermann et al. |
| 2007/0272763 A1* | 11/2007 | Dunne .................. A61M 11/02 239/8 |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0060640 A1 | 3/2008 | Waldner et al. |
| 2008/0083408 A1 | 4/2008 | Hodson et al. |
| 2008/0092885 A1 | 4/2008 | von Schuckmann |
| 2008/0156321 A1 | 7/2008 | Bowman et al. |

(56) References Cited

U.S. PATENT DOCUMENTS

| | | |
|---|---|---|
| 2008/0163869 A1 | 7/2008 | Nobutani et al. |
| 2008/0197045 A1* | 8/2008 | Metzger ............... B65D 75/327 206/539 |
| 2008/0249459 A1 | 10/2008 | Godfrey et al. |
| 2008/0264412 A1 | 10/2008 | Meyer et al. |
| 2008/0265198 A1 | 10/2008 | Warby |
| 2008/0283553 A1 | 11/2008 | Cox et al. |
| 2008/0299049 A1 | 12/2008 | Stangl |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0107873 A1* | 4/2009 | Cotton ................. B65D 75/327 206/531 |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0211576 A1 | 8/2009 | Lehtonen et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0012120 A1 | 1/2010 | Herder et al. |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1* | 7/2010 | Braithwaite ...... A61M 15/0028 604/403 |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2010/0313884 A1 | 12/2010 | Elliman |
| 2010/0331765 A1 | 12/2010 | Sullivan et al. |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0245780 A1 | 10/2011 | Helmer et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497059 A1 | 3/2004 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0811430 A1 | 3/1997 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1535643 A1 | 6/2005 |
| EP | 1595564 A1 | 11/2005 |
| EP | 1595822 A1 | 11/2005 |
| EP | 1521609 B1 | 12/2005 |
| EP | 1726324 A1 | 11/2006 |
| EP | 1736193 A1 | 12/2006 |

(56) References Cited

FOREIGN PATENT DOCUMENTS

| | | |
|---|---|---|
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 * | 1/2007 ............ A61M 15/00 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2002235940 A | 8/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 198100674 A1 | 3/1981 |
| WO | 198200785 A1 | 3/1982 |
| WO | 198300288 A1 | 2/1983 |
| WO | 198303054 A1 | 9/1983 |
| WO | 198605419 A1 | 9/1986 |
| WO | 198706137 A1 | 10/1987 |
| WO | 198803419 A1 | 5/1988 |
| WO | 198900889 A1 | 2/1989 |
| WO | 198900947 A1 | 2/1989 |
| WO | 198902279 A1 | 3/1989 |
| WO | 198903672 A1 | 5/1989 |
| WO | 198903673 A1 | 5/1989 |
| WO | 198905139 A1 | 6/1989 |
| WO | 199009780 A1 | 9/1990 |
| WO | 199009781 A1 | 9/1990 |
| WO | 1991014468 A1 | 10/1991 |
| WO | 199206704 A1 | 4/1992 |
| WO | 199217231 A1 | 10/1992 |
| WO | 199221332 A1 | 12/1992 |
| WO | 199222286 | 12/1992 |
| WO | 1993013737 A1 | 7/1993 |
| WO | 199325321 A1 | 12/1993 |
| WO | 1993024164 A1 | 12/1993 |
| WO | 1994007607 A1 | 4/1994 |
| WO | 199417822 A1 | 8/1994 |
| WO | 199425371 A1 | 11/1994 |
| WO | 9427653 A2 | 12/1994 |
| WO | 199503034 A1 | 2/1995 |
| WO | 1995032015 A1 | 11/1995 |
| WO | 9600050 A1 | 1/1996 |
| WO | 1996006011 A2 | 2/1996 |
| WO | 9606581 A1 | 3/1996 |
| WO | 199623522 A1 | 8/1996 |
| WO | 199701329 A1 | 1/1997 |
| WO | 199706813 A1 | 2/1997 |
| WO | 199706842 A1 | 2/1997 |
| WO | 199712683 A1 | 4/1997 |
| WO | 1997012687 A1 | 4/1997 |
| WO | 199720590 A1 | 6/1997 |
| WO | 199723208 A1 | 7/1997 |
| WO | 9727804 A1 | 8/1997 |
| WO | 199735562 A1 | 10/1997 |
| WO | 199741833 A1 | 11/1997 |
| WO | 1998012511 A2 | 3/1998 |
| WO | 199827959 A2 | 7/1998 |
| WO | 199831346 A1 | 7/1998 |
| WO | 199839043 A1 | 9/1998 |
| WO | 1999001227 A1 | 1/1999 |
| WO | 1999007340 A1 | 2/1999 |
| WO | 1999011563 A1 | 3/1999 |
| WO | 1999016530 A1 | 4/1999 |
| WO | 1999043571 A1 | 9/1999 |
| WO | 199962495 A2 | 12/1999 |
| WO | 199965464 | 12/1999 |
| WO | 200001612 A2 | 1/2000 |
| WO | 200023037 A1 | 4/2000 |
| WO | 2000023065 A2 | 4/2000 |
| WO | 200027543 A1 | 5/2000 |
| WO | 200037336 A1 | 6/2000 |
| WO | 2000033965 A1 | 6/2000 |
| WO | 200049988 A2 | 8/2000 |
| WO | 200064779 A1 | 11/2000 |
| WO | 200113885 A1 | 3/2001 |
| WO | 200128489 A1 | 4/2001 |
| WO | 2001064182 A2 | 9/2001 |
| WO | 200187392 A2 | 11/2001 |
| WO | 2001085097 A2 | 11/2001 |
| WO | 200197888 A2 | 12/2001 |
| WO | 200198175 A1 | 12/2001 |
| WO | 200198176 A2 | 12/2001 |
| WO | 200204054 A1 | 1/2002 |
| WO | 200205879 A1 | 1/2002 |
| WO | 200217988 A2 | 3/2002 |
| WO | 200232899 A1 | 4/2002 |
| WO | 2002034411 A1 | 5/2002 |
| WO | 2002070141 A1 | 9/2002 |
| WO | 2002089887 A1 | 11/2002 |
| WO | 2003002045 A1 | 1/2003 |
| WO | 2003014832 A1 | 2/2003 |
| WO | 2003020253 A2 | 3/2003 |
| WO | 2003022332 A2 | 3/2003 |
| WO | 2003035030 A1 | 5/2003 |
| WO | 2003037159 A1 | 5/2003 |
| WO | 2003037259 A2 | 5/2003 |
| WO | 2003049786 A2 | 6/2003 |
| WO | 2003050031 A1 | 6/2003 |
| WO | 2003053350 A2 | 7/2003 |
| WO | 2003057593 A1 | 7/2003 |
| WO | 2003059547 A1 | 7/2003 |
| WO | 2003068299 A1 | 8/2003 |
| WO | 2003087097 A1 | 10/2003 |
| WO | 2003097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 200433954 A1 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2004098795 A1 | 11/2004 |
| WO | 2005000476 A1 | 1/2005 |

(56) References Cited

FOREIGN PATENT DOCUMENTS

| | | |
|---|---|---|
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 200507997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007030162 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2010149280 A1 | 12/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A2 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013017640 A1 | 2/2013 |
| WO | 2013110601 A1 | 8/2013 |
| WO | 2013152861 A1 | 10/2013 |
| WO | 2013152894 A1 | 10/2013 |
| WO | 2014111370 A1 | 7/2014 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

"Activate". Collins English Dictionary, London: Collins, 2000, 2 pages. [Retrieved at http://search.credoreference.com/content/entry/hcengdict/activate/0 on Jun. 12, 2014].

"Lung Cancer". Merck Manual Home Edition, pp. 1-7. [Accessed at www.merck.com/mmhe/print/sec04/ch057/ch057a.html, on Jul. 28, 2010].

Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English for WO2009050978, 2009.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.

Ackermann et al.; Quantitative Online Detection of Low-Concentrated Drugs via a SERS Microfluidic System; ChemPhysChem; 2007; vol. 8; No. 18; pp. 2665-2670.

Beasley R et al: "Preservatives in Nebulizer solutions: Risks without Benefit" Pharmacotherapy, Boston, US, Bd. 18, Nr. 1, Jan. 1998.

Beasley R et al: "Preservatives in Nebulizer solutions: Risks without Benefit" Pharmacotherapy, Boston, US, Bd. 18, Nr. 1, Jan. 1998, pp. 130-139.

Bocci et al., "Pulmonary catabolism of interferons: alveolar absorption of 125I-labeled human interferon alpha is accompanied by partial loss of biological activity". Antiviral Research, vol. 4, 1984, pp. 211-220.

Chen, F-K et al., "A study of forming pressure in the tube-hydroforming process". Journal of Materials Processing Technology, 192-193, 2007, p. 404-409.

China Suppliers, Shanghai Lite Chemical Technology Co., Ltd. Product details on polyvinylpyrrolidones. Obtained online by the USPTO examiner on Apr. 24, 2011.

Cras et al., "Comparison of chemical cleaning methods of glass in preparation for silanization". Biosensors & Bioelectronics, vol. 14, 1999, pp. 683-688.

Diamond et al., "Substance P Fails to Mimic Vagally Mediated Nonadrenergic Bronchodilation". Peptides, vol. 3, 1982, pp. 27-29.

Elwenspoek et al., "Silicon Micromachining", Chapter 3, Mechanical Microsensors, Springer-Verlag Berlin Heidelberg, 2001, 4 pages.

English Language Abstract of EP1068906, 2001.

Fuchs et al., "Neopterin, biochemistry and clinical use as a marker for cellular immune reactions". International Archives of Allergy and Immunology, vol. 101, No. 1, 1993, pp. 1-6, Abstract 1p.

Han et al.; Surface activation of thin silicon oxides by wet cleaning and silanization; Thin Solid Films; 2006; vol. 510; No. 1-2; pp. 175-180.

(56) References Cited

OTHER PUBLICATIONS

Henkel et al.; Chip modules for generation and manipulation of fluid segments for micro serial flow processes; Chemical Engineering Journal; 2004; vol. 101; pp. 439-445.

Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.

Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.

IP et al., "Stability of Recombinant Consensus Interferon to Air-Jet and Ultrasonic Nebulization". Journal of Pharmaceutical Sciences, vol. 84, No. 10, Oct. 1995, pp. 1210-1214.

Jendle et al., "Intrapulmonary administration of insulin to healthy volunteers". Journal of Internal Medicine, vol. 240, 1996, pp. 93-98.

JP2005144459—English language abstract only.

Kutchoukov et al., "Fabrication of nanofluidic devices using glass-to-glass anodic bonding" Sensors and Actuators A, vol. 114, 2004, pp. 521-527.

Lougheed et al., "Insulin Aggregation in Artificial Delivery Systems". Diabetologia, vol. 19, 1980, pp. 1-9.

Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).

Niven et al., "Some Factors Associated with the Ultrasonic Nebulization of Proteins". Pharmaceutical Research, vol. 12, No. 1, 1995, pp. 53-59.

Remington Pharmacy, Editor Alfonso R. Gennaro. 19th ed., Spanish Secondary Edition: Panamericana, Spain, 1995, Sciarra, J. J., "Aerosols", pp. 2560-2582. The English translation is from the 1995 English Primary Edition, Sciarra, J. J., Chapter 95, R97-1185.

Trasch et al., "Performance data of refloquant Glucose in the Evaluation of Reflotron". Clinical Chemistry, vol. 30, 1984, p. 969.

Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.

Wang et al.; Self-Assembled Silane Monolayers: Fabrication with Nanoscale Uniformity; Langmuir; 2005; vol. 21; No. 5; pp. 1848-1857.

Abstract in English for JP2002-235940, 2001.

\* cited by examiner

DISPENSING DEVICE, STORAGE DEVICE AND METHOD FOR DISPENSING A FORMULATION

FIELD OF THE INVENTION

The present invention relates to a dispensing device for dispensing a medical formulation, preferably dry powder inhalers for the delivery of drugs to the lungs.

BACKGROUND OF THE INVENTION

Drugs delivered through dispensing devices, in particular inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles or droplets. As currently believed to be understood, particles having an aerodynamic diameter of less than 2 µm are considered to be potentially optimal for deposition in the alveolar region of the lung. Particles that have an aerodynamic diameter of between 2 and approximately 5 µm may be more suitable for delivery to the bronchiole or bronchi regions. Particles with an aerodynamic size range greater than 6 µm, and more preferably 10 µm, are typically suitable for delivery to the laryngeal region, throat or nasal passages.

In most cases, it is desired to achieve a high inhalable fraction and a high delivery efficiency, i.e. the fraction of the initial dose of drug that reaches the desired region, in particular in the lung. This depends on various factors, in particular on the characteristics of the generated spray plume, such as propagation velocity of the plume, particle size and its distribution, fraction of small particles, fraction of gas or the like. In the present invention, the desired spray plume characteristics include preferably a small particle size, a high fraction of drug particles with a diameter of 6 µm or less, a low propagation velocity and/or a long duration of spray generation and possible inhalation.

In the following, the description will focus mainly on powder formulations. However, the same applies for liquid formulations.

Many dry powder inhalers are on the market or have been proposed. There are two main types, namely the passive ones and the active ones. In passive inhalers all the energy required for de-agglomerating the powder and transferring the powder to the lungs is provided by the breathing of a user, respectively the patient. In active inhalers there is an additional source of energy to help to de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependent on the breathing of the patient. The de-agglomeration of the powder and hence the inhalable fraction is a function of the flow rate of inhaled air through the device and, therefore, varies greatly from patient to patient.

Dry powder inhalers are subdivided into single dose and multi-dose devices or inhalers. Multi-dose inhalers are further subdivided into pre-metered types where the doses are stored individually and into metering inhalers where each powder dose is metered in the device.

Multi dose pre-metered inhalers have the advantage that the single doses are metered under strict factory conditions and the powder can quite easily be isolated from the atmosphere. In many applications the active drug powder is mixed with a carrier such as lactose which tends to absorb humidity from the atmosphere which makes it stick together and difficult to de-agglomerate.

U.S. Pat. No. 4,627,432 A discloses a device for administering medicaments to patients, namely an inhaler. The inhaler comprises a disk-like blister pack having a plurality of blister pockets arranged in a circle. Each blister pocket contains a dose of the powder. A plunger can open a blister pocket. When a blister is opened, the medicament can be withdrawn by a patient inhaling through a mouthpiece.

It is difficult to empty the respective blister pocket completely during a dispensing operation. Incomplete emptying results in decreased delivery efficiency. Some powder may be lost in the inhaler and not dispensed because the known solutions require relatively long paths for the powder until the powder reaches a nozzle and is actually dispensed. This might reduce the delivery efficiency further. In addition, de-agglomeration of the powder is difficult and the powder may block an outlet nozzle that is used for dispensing multiple doses one after the other.

WO 2007/062721 A1, which forms the starting point of the present invention, discloses a dispensing device for dispensing a preferably medical formulation as a spray. The dispensing device is adapted to receive or comprises a storage device. The storage device comprises a carrier with multiple cavities. Each cavity comprises a moveable insert. Each insert comprises a storage chamber with a dose of the formulation, and a duct for dispensing the respective dose. The cavities are sealed. The sealings can be opened by pushing the respective insert through the associated sealing. Then, the respective dose is dispensed by pressurized air supplied to the insert.

Object of the present invention is to provide an improved dispensing device, storage device and method for dispensing a preferably medical formulation, in particular wherein a very simple design of the storage device and/or simple opening of the storage device can be achieved.

The above object is achieved by a dispensing device, by a storage device or by a method as disclosed and described herein.

SUMMARY OF THE INVENTION

As noted above, the present invention relates to a dispensing device for dispensing a medical formulation, preferable dry powder inhalers for the delivery of drugs to the lungs. In particular, the present invention relates to an active, gas (preferably air) powered, pre-metered multi-dose dispensing device for dispensing a formulation containing or consisting of a drug, such as a dry powder inhaler.

In one embodiment, the invention relates to a dispensing device (1) for dispensing a preferably medical formulation (2) ("the dispensing device of the invention"), in particular containing or consisting of a drug, as a spray (3), wherein the dispensing device (1) is adapted to receive or comprises a storage device (4), the storage device (4) comprising a carrier (5) with multiple storage members (6), each storage member (6) comprising a storage cavity (9) containing a dose of the formulation (2), and a duct (10) or nozzle (11) for dispensing the respective dose in a dispensing direction (12).

In another embodiment, the invention relates to a device as described in the embodiment immediately above, characterized in that the formulation (2) is a liquid, in particular a solution, suspension or solution.

In another embodiment, the invention relates to a device as described in the embodiment immediately above, characterized in that the formulation (2) is a powder.

In another embodiment, the invention relates to a device as described in any of the above embodiments, characterized in that the carrier (5) is flexible and/or band-like and/or is a blister, preferably a blister strip.

In another embodiment, the invention relates to a device as described in any of the above embodiments, characterized in that the carrier (5) comprises the base layer (7) and the peelable cover layer (8), wherein the storage members (6) are inserted or held between these layers (7, 8) before and/or during dispensing.

In another embodiment, the invention relates to a device as described in any of the above embodiments, characterized in that the storage members (6) are parts made separately from the carrier (5).

In another embodiment, the invention relates to a device as described in any of the first four embodiments above, characterized in that the storage members (6) are formed by the carrier (5), in particular the base layer (7) and the cover layer (8) of the carrier (5).

In another embodiment, the invention relates to a device as described in any of the above embodiments, characterized in that each storage member (6) is a molded element, a cartridge, a capsule or a container.

In another embodiment, the invention relates to a device as described in any of the above embodiments, characterized in that each storage member (6) is rigid or flexible.

In another embodiment, the invention relates to a device as described in any of the above embodiments, characterized in that the dispensing device (1) comprises an opening, connecting and/or supply means (14), in particular a piercing element (15), such as a needle, for opening or piercing the storage members (6) individually and/or supplying pressurized gas to the respective storage member (6) to dispense the respective dose.

In another embodiment, the invention relates to a device as described in any of the above embodiments, characterized in that the dispensing device (1) comprises means for providing pressurized gas, in particular air, for dispensing the formulation (2), preferably wherein the dispensing device (1) comprises a preferably manually operated air pump (13) as means for providing pressurized gas.

In another embodiment, the invention relates to a device as described in any of the above embodiments, characterized in that the dispensing device (1) is designed such that the carrier (5) can be moved or indexed stepwise from one storage member (6) to the next storage member (6).

In another embodiment, the invention relates to a device as described in any of the above embodiments, characterized in that the dispensing device (1) is a preferably oral inhaler, in particular a dry powder inhaler.

In another embodiment, the invention relates to a device as described in any of the above embodiments, characterized in that the storage members (6), ducts (10) or nozzles (11) are sealed by one common sealing or cover layer (8).

In another embodiment, the invention relates to a storage device (4) for a preferably medical formulation (2) ("the storage device of the invention"), in particular containing or consisting of a drug, preferably for a dispensing device (1) as described in any of the embodiments above, the storage device (4) comprising a carrier (5) with multiple storage members (6), each storage member (6) comprising a storage cavity (9) containing a dose of the formulation (2), and a duct (10) or nozzle (11) for dispensing the respective dose in a dispensing direction (12), characterized in that the dispensing direction (12) of the ducts (10) or nozzles (11) is directed in a lengthwise direction of the storage device (4) or carrier (5), and/or that the storage device (4) or carrier (5) is a peelable blister strip, wherein the ducts (10) or nozzles (11) can be opened one after the other by peeling the blister strip, and/or that the carrier (5) carries the storage members (6) formed separately from the carrier (5) rigidly or in a unmovable manner and is adapted that the storage members (6), the ducts (10) or the nozzles (11) can be opened without movement of the storage members (6) or a base layer (7) thereof by opening or peeling a preferably common feeling or cover layer (8).

In another embodiment, the invention relates to storage device of the invention, characterized in that the formulation (2) is a liquid, in particular a solution, suspension or suslution.

In another embodiment, the invention relates to storage device of the invention, characterized in that the formulation (2) is a powder.

In another embodiment, the invention relates to storage device of the invention as described in the three embodiments immediately above, characterized in that the carrier (5) is flexible and/or band-like.

In another embodiment, the invention relates to storage device of the invention as described in the four embodiments immediately above, characterized in that the carrier (5) comprises a base layer (7) and a peelable cover layer (8), wherein the storage members (6) are inserted or held between these layers (7, 8) before and/or during dispensing.

In another embodiment, the invention relates to storage device of the invention as described in the five embodiments immediately above, characterized in that the storage members (6) are parts made separately from the carrier (5).

In another embodiment, the invention relates to storage device of the invention as described in the first four storage device embodiments above, characterized in that the storage members (6) are formed by the carrier (5), in particular a base layer (7) and a cover layer (8) of the carrier (5).

In another embodiment, the invention relates to storage device of the invention as described in the seven embodiments immediately above, characterized in that each storage member (6) is a molded element, a cartridge, a capsule or a container.

In another embodiment, the invention relates to storage device of the invention as described in the eight embodiments immediately above, characterized in that each storage member (6) is rigid or flexible.

In another embodiment, the invention relates to storage device of the invention as described in the five embodiments immediately above, characterized in that the storage members (6), ducts (10) or nozzles (11) are sealed by one common sealing or cover layer (8).

In another embodiment, the invention relates to a method for dispensing a preferably medical formulation (2) ("the dispensing method of the invention"), in particular containing or consisting of a drug, as a spray (3) from a blister strip comprising with multiple storage members (6), each storage member (6) comprising a storage cavity (9) containing a dose of the formulation (2), and a duct (10) or nozzle (11) for dispensing the respective dose, characterized in that the blister strip is peeled to open the storage members (6), the ducts (10) or the nozzles (11) one after the other so that the doses can be dispensed one after the other.

In another embodiment, the invention relates to storage device of the invention as described in the embodiment immediately above, characterized in that the storage members (6), ducts (10) or nozzles (11) are sealed by one common sealing or cover layer (8), wherein the common sealing or cover layer (8) is peeled.

In another embodiment, the invention relates to storage device of the invention as described in the two embodiments immediately above, characterized in that the storage members (6) are individually connected to a supply of pressurized gas, in particular by piercing the respective storage member (6) by means of a piercing element (15).

In another embodiment, the invention relates to storage device of the invention as described in the three embodiments immediately above, characterized in that the doses are individually subjected to a gas pressure for dispensing.

In another embodiment, the invention relates to storage device of the invention as described in the embodiment immediately above, characterized in that air is pressurized and used as gas, in particular wherein air is pressurized by manually operating an air pump (13).

In one embodiment, the medical formulation described in any of the embodiments above contains a drug or mixture of drugs.

In another embodiment, the medical formulation described in any of the embodiments above consists of a drug or mixture of drugs.

The term "formulation" relates in particular to powder, but may include or relate to liquid as well. Consequently, the fine "particles" may be either solid or liquid. The term "liquid" has to be understood preferably in a broad sense covering inter alia solutions, suspensions, suslutions, mixtures thereof or the like. More particularly, the present invention relates to the dispensing of formulations for inhalation, such as medical formulations containing or consisting of at least one drug.

According to a first aspect of the present invention, the dispensing direction of the ducts or nozzles of storage members located on a carrier is directed at least essentially in a lengthwise or indexing direction of the storage device or carrier. This allows in particular a very simple construction and/or opening.

According to a second aspect of the present invention, the storage device or carrier is a peelable blister strip, wherein the ducts or nozzles can be opened one after the other by peeling the blister strip. This allows a very simple construction and/or opening.

According to a third aspect of the present invention, the storage members are separate parts that are fixed on the carrier and cannot be moved relatively to the carrier. The storage members or its ducts or nozzles are closed by a preferably common sealing or cover layer. The storage members, ducts or nozzles can be opened one after the other by opening or peeling the sealing or cover layer. This allows a very simple construction and/or opening.

It has to be noted that each storage member preferably comprises an individual duct or nozzle for dispensing the respective dose. In particular, a spray is directly or only to formed by or directly after the duct or nozzle. The duct or nozzle may dispense the generated spray in to a mouthpiece for inhalation by a user or patient. However, any further spray forming means is preferably not provided.

BRIEF DESCRIPTION OF THE DRAWINGS

Further aspects, advantages and features of the present invention will be apparent from the claims and following detailed description of preferred embodiments. In the drawings show:

In the Fig., the same reference signs are used for same or similar components, wherein same or similar characteristics, features or advantages are or can be realized or achieved even if a repeated discussion is omitted. Further, the features and aspects of the different embodiments can be combined in any desired manner and/or used for other dispensing devices or methods for dispensing in particular medical formulations for inhalation.

DETAILED DESCRIPTION OF THE INVENTION

Figure 1:
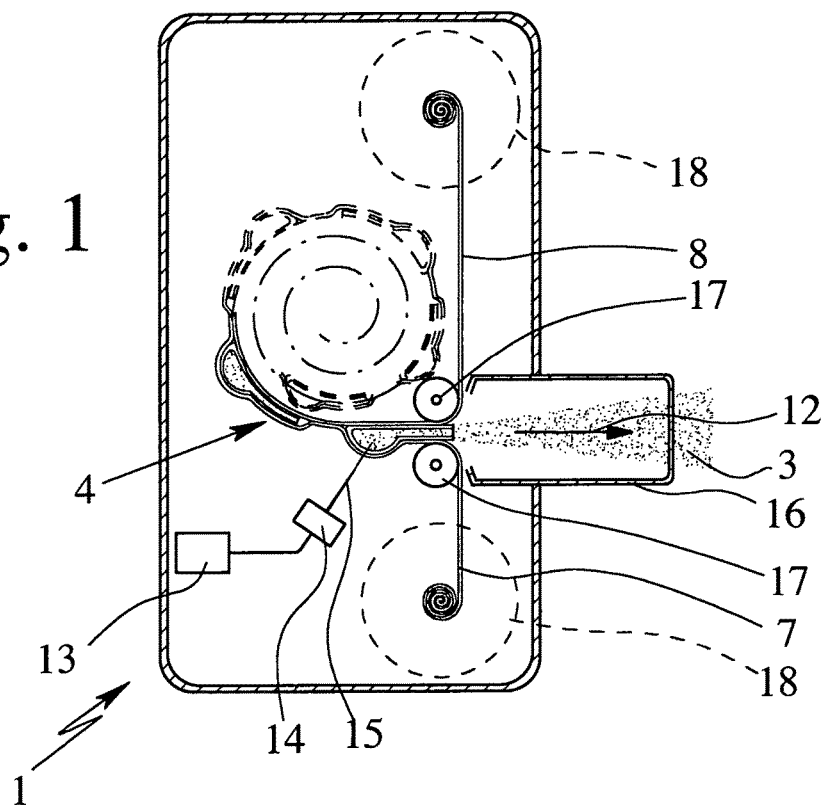
FIG. 1 a schematic sectional view of a dispensing device with a storage device according to the present invention during dispensing.

FIG. 1 shows in a schematic sectional view—for illustration purposes not in scale—a dispensing device 1 according to the present invention. The dispensing device 1 is an active device, in particular gas powered. Here, the dispensing device 1 is a preferably oral or nasal inhaler, in particular a dry powder inhaler, for a user, respectively the patient (not shown).

The dispensing device 1 may be used for dispensing any formulation 2 as defined in the introductory part of the description. In particular, a medical formulation 2 or a formulation 2 for inhalation will be used. The formulation 2 preferably contains or consists of at least one drug. When the formulation 2 is dispensed, a spray 3 is generated as indicated in FIG. 1. The spray 3 includes fine particles (solid and/or liquid) of the formulation 2 and preferably has the desired spray plume characteristics.

The formulation 2 may be a liquid, in particular a solution, a suspension or any mixture thereof, i.e. a so-called suslution. Preferably, when different drugs are dispensed simultaneously, a suslution may be used. The principle of the suslution is based on that different drugs may be combined in one formulation simultaneously as a solution and as a suspension. In this respect, reference is made to EP 1 087 750 A1 which is incorporated herein as additional disclosure in this respect.

Preferably, the formulation 2 is a powder. The powder may be a pure drug or a mixture of at least two drugs. In addition, the powder may contain at least one other material, in particular a drug carrier such as lactose. In the following, the description focuses on powder as formulation 2. However, the description applies in a similar manner if a liquid formulation 2 is used.

Preferably the mean diameter of the powder particles is about 2 to 7 μm, in particular 6 μm or less. This applies in particular if the powder does not contain any drug carrier such as lactose.

If the powder contains a drug carrier, such as lactose, and at least one drug, the powder 2 may have a particle size of 20 to 300 μm, in particular about 30 to 60 μm. However, the de-agglomeration, which will be described later in more detail, may result even in this case in a spray 3 with a smaller particle size, e.g. of about 10 μm or less. In particular, the drug may be separated from the drug carrier during de-agglomeration so that primarily the drug will be inhaled due to its small particle size of about 2 to 6 μm and the larger drug carrier will be swallowed when using the dispensing device as an inhaler. Alternatively or additionally, breaking or opening of the drug carrier is possible during de-agglomeration.

The diameters mentioned above and below may be understood as mass medium aerodynamic diameters and/or may apply to the particle size or a fraction of the particles of the spray 3.

The dispensing device 1 is adapted to receive or comprises a storage device 4 for storing preferably multiple and pre-metered doses of the formulation 2. The storage device 4 may be integrated into the dispensing device 1 or form part of the dispensing device 1. Alternatively, the storage device 4 may be a separate part that can be inserted or connected with the dispensing device 1 and optionally replaced.

Figure 2:
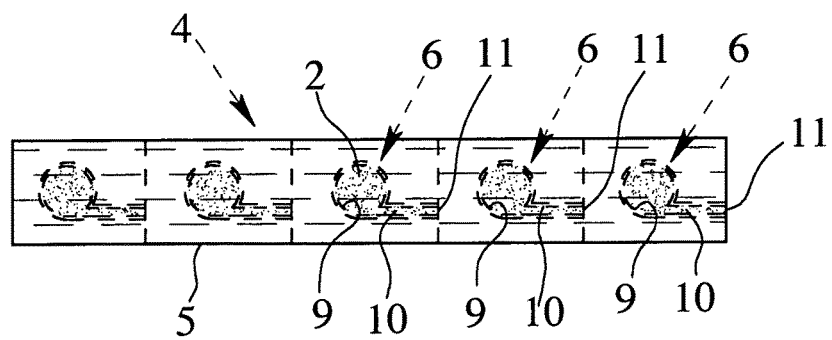
FIG. 2 a top view of a part of the storage device with multiple storage members.

The storage device 4 comprises a carrier 5 with storage members 6, as shown also in the top view of FIG. 2 of a part of the storage device 4. In particular, the carrier 5 may comprise 20 to 100, preferably 30 to 60 storage members 6. Each storage member 6 contains preferably one pre-metered dose of the formulation 2. However, each storage member 6 may also contain more than one formulation 2, i.e. different formulations 2. Additionally or alternatively, different storage members 6 may contain different formulations 2. In the present invention, "different" means in particular that the formulations 2 differ in at least one of the composition, the drug, the dose or amount, the concentration, and consistence of the formulation 2, e.g. liquid or dry or powder.

The storage device 4 or carrier 5 is preferably a blister strip.

Figure 3:
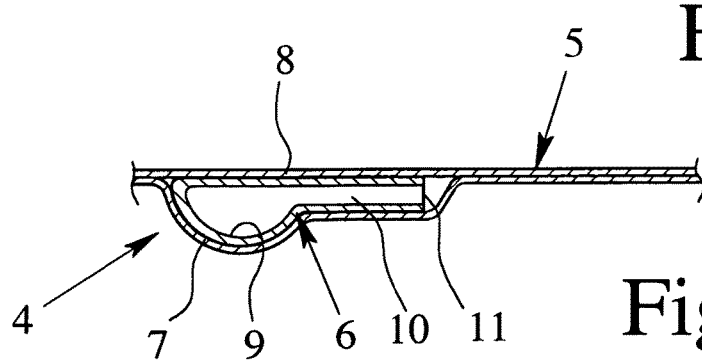
FIG. 3 a schematic sectional view of a part of the storage device with one storage member.
Figure 4:
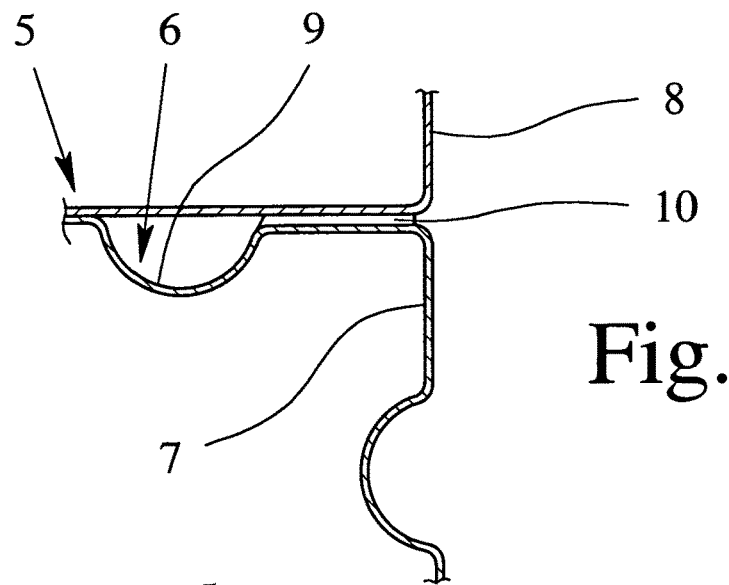
FIG. 4 a schematic sectional view of a part of the storage device according to an other embodiment.
Figure 5:
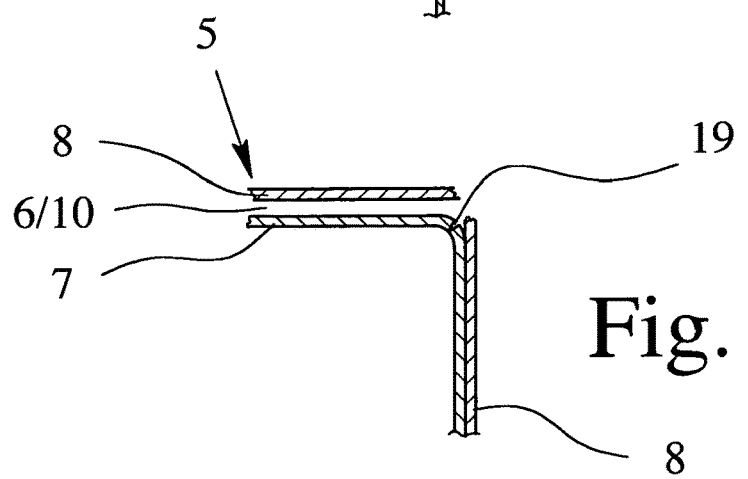
FIG. 5 a schematic sectional view of a part of the storage device according to a further embodiment.
Figure 6:
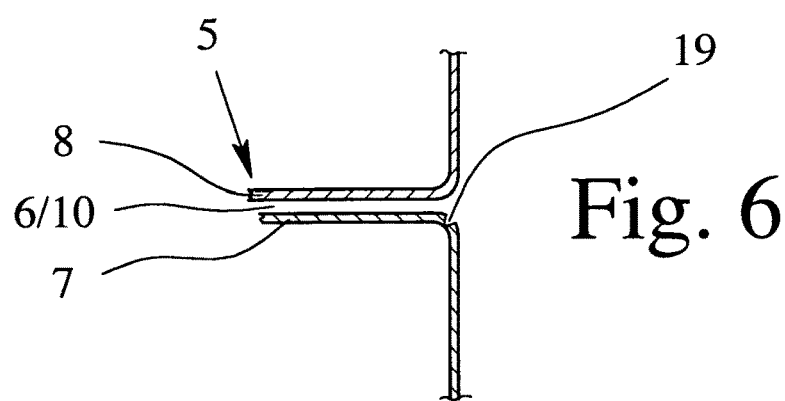
FIG. 6 a schematic sectional view of a part of the storage device according to still an other embodiment.
Figure 7:
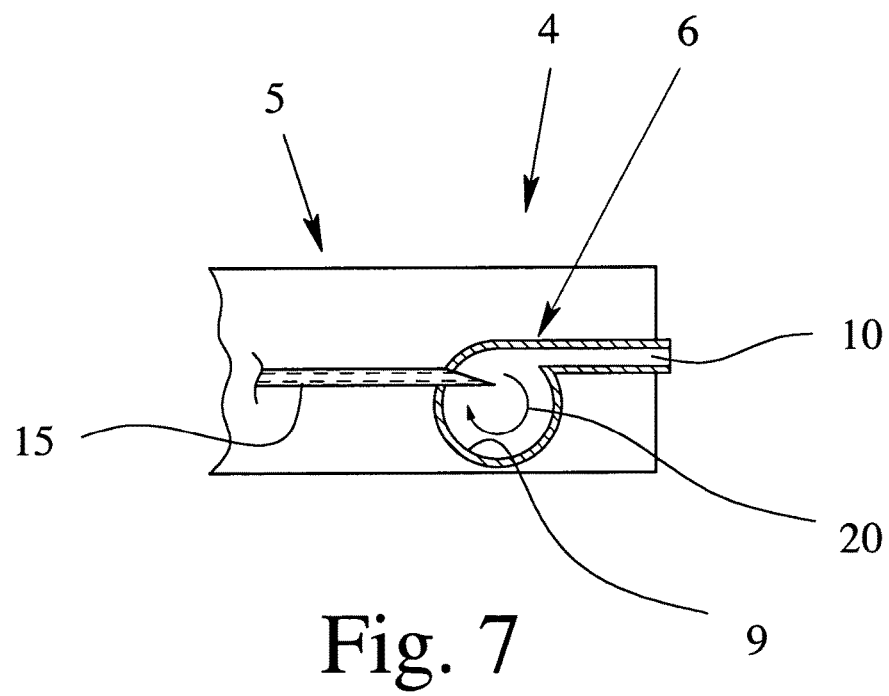
FIG. 7 a schematic sectional view of a part of the storage device shown in FIGS. 1 to 3 when pierced to discharge a formulation.
Figure 8:
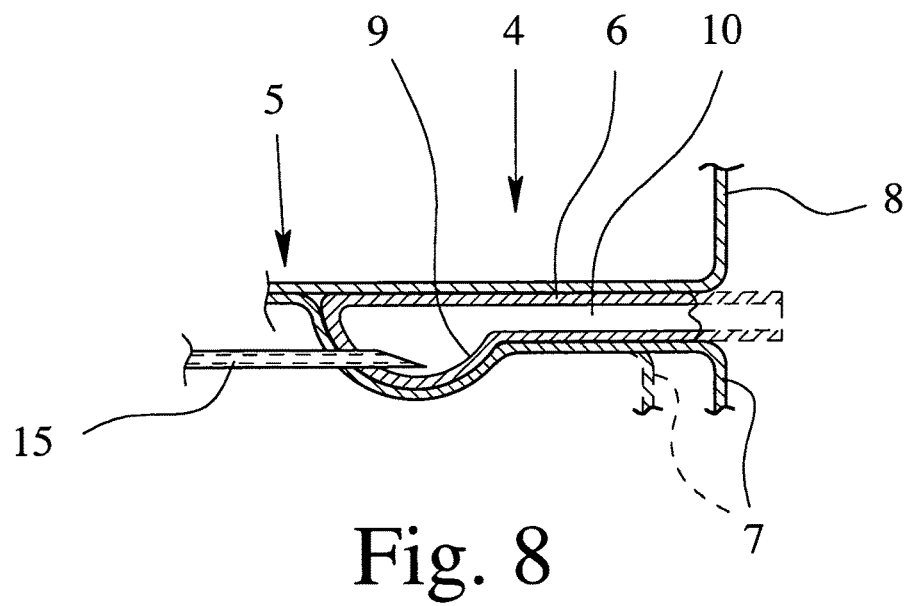
FIG. 8 a sectional view perpendicular to FIG. 7.

In the present embodiment, the carrier 5 comprises a base layer 7 and a sealing or cover layer 8, as shown in FIG. 3 representing a schematic sectional, longitudinal view of a part of the storage device 4 with one storage member 6.

In the present embodiment, the storage members 6 are preferably formed or made as separate parts. In particular, the storage members 6 are mounted or fixed on the carrier 5 or inserted or held between the two layers 7 and 8 before and/or during dispensing.

Before use or opening, the storage members 6 are sealed by the base layer 7 and/or cover layer 8. In the present embodiment, the base layer 7 is indented and/or follows the contour of the preferably bulky storage members 6. The storage members 6 preferably end at least essentially flat in the main plane of the base layer 7. The cover layer 8 is preferably flat and forms a sealing or cover so that the storage members 6 are sealed from each other and/or hermetically against the atmosphere.

The base layer 7 may be formed by any suitable material, in particular plastic or the like, most preferably by any suitable composite material.

The cover layer 8 may be formed by any suitable material, in particular aluminum foil, a composite foil or any other suitable material.

However, other constructions are possible. In particular, the base layer 7 may be flat and the cover layer 8 may be indented. Alternatively, both layers 7 and 8 may be indented and/or non-flat.

Alternatively or additionally, the layers 7 and 8 and/or other parts of the carrier 5 may form the storage members 6.

The storage device 4, carrier 5 or blister strip is preferably longitudinal and/or band-like.

In particular, the storage members 6 are located one after the other in a row and spaced in lengthwise or longitudinal direction of the storage device 4, carrier 5 or blister strip.

Preferably, each storage member 6 is made of foil, plastics, ceramics and/or composite material, in particular of thermoplastics or thermoplastic elastomers and for sealings of elastomers or silicone.

Each storage member 6 may form a preferably block-like unit and be rigid. Alternatively, the storage members 6 may be flexible. In particular, each storage member 6 may be a unitary unit or consists of multiple elements. Each storage member 6 may be a molded element, a cartridge, a blister, a capsule, a container or the like.

In the following, a preferred construction of one storage member 6 is explained. Preferably, all storage members 6 are identical. However, it is also possible that all or some storage members 6 are different. For example, two or more groups of different storage members 6 can be provided. It is possible that one group has a different dose or different formulation 2 than the other group. For example, the storage members 6 of the different groups could be arranged alternately one after the other so that a patient or user may use for example each morning a storage member 6 of one group and each evening a storage member 6 of the other group.

Each storage member 6 comprises a storage chamber 9 for the formulation 2.

Each storage member 6 further comprises a duct 10 or the like for discharging the formulation 2 during the dispensing operation. The formulation 2 is dispensed through the duct 10 during the dispensing operation, in particular for de-agglomerating the powder and/or forming the spray 3.

The duct 10 can comprise or form a nozzle 11 preferably at the outlet. Alternatively, the nozzle 11 or any other suitable nozzle arrangement could be used instead of or in any other combination with duct 10.

Preferably, the duct 10/nozzle 11 is formed integrally with the storage chamber 9 and/or by a base member of the storage member 6, in particular by a recess, grove or the like in the base member 11, and by an associated cover member of the storage member 6. In particular, the duct 10 forms a channel from the storage chamber 9 to an outlet of the storage member 6 for discharging the formulation 2 as spray 3 as shown in FIG. 1.

Preferably, the duct 10/nozzle 11 dispenses the dose of formulation 2 of the respective storage member 6 in a dispensing direction as indicated by arrow 12 in FIG. 1.

Preferably, the dispensing direction 12, the duct 10 and/or the nozzles 11 are directed in a lengthwise or indexing direction of the storage device 4/carrier 5/blister strip. This allows a very simple and compact design of the dispensing device 1 and/or storage device 4.

Preferably, the storage members 6/ducts 10/nozzles 11 are opened one after the other—i.e. individually—by peeling the blister strip, in particular the cover layer 8 and/or base layer 7, so that the respective doses of the formulation 2 can be dispensed one after the other.

Preferably, the formulation 2 is dispensed by gas pressure, in particular air pressure (active inhaler). However, it is also possible to dispense the formulations 2 by means of an air stream generated by breathing in of a user or patient (not passive inhaler).

In the present embodiment, the dispensing device 1 uses pressurized gas to force the formulation 2 through the duct 10/nozzle 11 to de-agglomerate the powder and/or to generate the spray 3. Preferably, the dispensing device 1 comprises a means for providing pressurized gas, in the present embodiment an air pump 13 which can preferably be actuated or operated manually. In particular, the air pump 13 comprises or is formed by a bellows. But, it could be also a piston-cylinder-arrangement. Instead of the air pump 13, the means for providing pressurized gas can be e.g. a capsule, container or the like containing pressurized or liquefied gas for powering the dispensing device 1, i.e. dispensing the formulation 2 as desired.

The air pump 13 may provide a gas pressure of less than 300 kPa, in particular about 50 to 200 kPa. This is preferably sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular the storage chamber 9 of the respective storage member 6.

Preferably, all pressure values mentioned in the present description are gauge pressures, i.e. pressure differences. All pressure values relate to the pressure in a gas storage such as a container with pressurized or liquefied gas or provided by air pump 13 or relate to the pressures acting in the storage chamber 9 and/or in the duct 10.

FIG. 1 shows schematically that the dispensing device 1 comprises a mechanism 14 for connecting the storage members 6 individually to the gas supply, in particular to the air pump 13. The mechanism 14 comprises preferably a piercing element 15, such as a hollow needle, or any other suitable connecting element.

The connecting mechanism 14 is preferably designed such that it open 5 or pierces the storage chamber 9 of the storage members 6 that shall be emptied next. In particular, the piercing element 15 can penetrate the base layer 7 and/or cover layer 8 and the wall of the storage chamber 9 so that gas can be supplied into the storage chamber 9 to generate a gas stream which entrains the formulation 2 in the storage chamber 9 and dispenses the formulation 2 through the duct 10/nozzle 11 and generates the spray 3 as schematically shown in FIG. 1.

Actuation and/or movement of the connecting mechanism 14 and/or piercing element 15 can be combined with the actuation of the means for pressurizing gas (air pump 13) or operated separately.

Preferably the storage chamber 9 forms a mixing chamber for mixing the gas with the powder. The chamber 9 is preferably designed such that the gas can generate swirls or eddies for better mixing the powder with the gas. Preferably, the chamber 9 is substantially circular in cross section, in particular cylindrical. However, other shapes are also possible.

Further, the chamber 9 is formed with no sharp edges, corners or the like, but has a smooth contour so that the gas can sweep all chamber surfaces to prevent powder accumulating on said surfaces and to ensure or allow complete discharge of the powder. In particular, the gas inlet formed by the piercing element 15 or any other supply element is located opposite to the outlet, i.e. duct 10 and/or nozzle 11, with regard to the axial or outlet direction.

The duct 10 is preferably at least essentially tangentially connected to the storage chamber 9 in the embodiment. Preferably, the duct 10 is connected at one axial end of the preferably cylindrical chamber 9, and the gas inlet is inserted to the other axial end of the chamber 9. In particular, the gas inlet is connected also tangentially to the storage chamber 10, such that swirls are generated when entering the gas with a swirl direction supporting discharge of the mixture of gas and formulation 2 through the duct 10 which connects tangentially to the rotational direction of the swirl.

During the dispensing operation, the spray 3 is preferably directly generated by the respective storage member 6 or its duct 10/nozzle 11 and outputted into a mouthpiece 16 of the dispensing device 1 as shown in FIG. 1 for inhalation by a patient or user (not shown).

The powder will be discharged—in particular forced through the duct 10—with a comparatively low gas pressure (preferably less than 300 kPa, in particular about 50 to 200 kPa). This low gas pressure which is significantly lower than the gas pressures in the prior dispensing devices enables a respectively low discharge velocity and, therefore, a low spray 3 with slow propagation velocity.

After dispensing one dose or for dispensing the next dose, the piercing element 15 will be withdrawn from the connected storage member 6. During this opposite movement or by a separate actuation or during the movement for connecting the next storage member 6 to the gas supply, the carrier 5 will be indexed one step further to the next storage member 6.

In the shown embodiment, the carrier 5, base layer 7 and/or cover layer 8 may be used to feed or index or move the storage device 4 from one storage member 6 to the next storage member 6.

In particular, the base layer 7 and/or cover layer 8 can be peeled or pulled, preferably in at least essentially opposite directions or in directions inclined to each other. The storage device 4/carrier 5 and/or layers 7 or 8 may be guided by guide rollers 17 or any other suitable guiding elements and/or wound up by suitable mechanisms, in particular spooling devices 18 or the like.

Preferably, the pooling of the carrier 5 and/or of the base layer 7 and/or cover layer 8 is preferably the only drive to index the storage device 4 one step further or to the next storage member 6. However, other constructional solutions are possible as well.

The unused storage device 4 may be wound up in the dispensing device 1, e.g. together with the carrier 5, in particular base layer 7.

According to another (not shown) embodiment, the duct 10 can also be used as a reservoir (storage chamber 9) for the formulation 2. In this case, the separate storage chamber 9 is not required. Then, the duct 10 is designed to enable sufficient mixing of the gas with the formulation 2 and sufficient de-agglomeration of the powder formulation 2.

Preferably, the spray 3 has a mean velocity (taken 20 cm from the outlet 15 or mouthpiece 16) of less than 2 m/s, in particular less than 1 m/s. Preferably, the mean duration of the spray 3 is at least 0.2 or 0.3 s, in particular about 0.5 to 2 s.

According to another embodiment, a secondary packaging may be used for packing and protecting the storage device 4/carrier 5, in particular for storage purposes before storage membering the storage device 4/carrier 5 into the dispensing device 1. Additionally the whole device 1 including storage device 4/carrier 5 may be stored in a secondary water vapor proof packaging.

According to a further embodiment, the dispensing devise 1 may be breath activated, in particular wherein the formulation 2 is only released after the patient's or user's inhalation rate has reached a predetermined level, preferably by the use of a pressure sensitive means, such as a bursting element, membrane or valve, or any other mechanism.

LIST OF REFERENCE NUMBERS

1 dispensing device
2 formulation 3 spray
4 storage device
5 carrier
6 storage member
7 base layer
8 cover layer
9 storage chamber
10 duct
11 nozzle
12 dispensing direction
13 air pump
14 connecting mechanism
15 piercing element
16 mouthpiece
17 guide roller
18 spooling device

What is claimed is:

1. A dry powder inhaler (1) for dispensing a medical powder formulation (2) containing a drug, as a powder spray (3), wherein the medical powder formulation (2) contains a drug, and wherein the dry powder inhaler (1) comprises:
a storage device (4) including a carrier (5) having multiple storage members (6) in a flexible, band-like arrangement, wherein each of said multiple storage members (6) includes: (i) a respective storage cavity (9) containing a dose of the medical powder formulation (2), and (ii) a respective nozzle (11) having an outlet oriented such that the medical powder dose is dispensed from the respective storage cavity (9), through the respective nozzle, and outward from the outlet in a dispensing direction (12), characterized in that the respective nozzle (11) includes a duct (10) that forms a channel from the storage cavity (9) to the outlet, where the duct (10) is formed integrally with the storage cavity (9), and the dispensing direction (12) of the respective nozzle (11) is directed at least in a lengthwise or indexing direction of the carrier (5).

2. The dry powder inhaler according to claim 1, characterized in that the carrier (5) is a blister strip.

3. The dry powder inhaler according to claim 1, characterized in that the carrier (5) comprises a base layer (7) and a peelable cover layer (8), wherein the multiple storage members (6) are inserted or held between these layers (7, 8) before and/or during dispensing.

4. The dry powder inhaler according to claim 1, characterized in that the multiple storage members (6) are parts made separately from the carrier (5).

5. The dry powder inhaler according to claim 1, characterized in that the multiple storage members (6) are formed by the carrier (5), a base layer (7) and a cover layer (8) of the carrier (5).

6. The dry powder inhaler according to claim 1, characterized in that each of the multiple storage members (6) is a molded element, a cartridge, a capsule or a container.

7. The dry powder inhaler according to claim 1, characterized in that each of the multiple storage members (6) is rigid or flexible.

8. The dry powder inhaler according to claim 1, characterized in that the dry powder inhaler (1) further comprises an opening, connecting and/or supply means (14), a piercing element (15) for opening or piercing the multiple storage members (6) individually and/or supplying pressurized gas to each of the multiple storage members (6) to dispense the dose from each of said multiple storage members (6).

9. The dry powder inhaler according to claim 1, characterized in that the dry powder inhaler (1) further comprises a means for providing pressurized gas for dispensing the medical powder formulation (2), wherein the dry powder inhaler (1) comprises a manually operated air pump (13) as means for providing pressurized gas.

10. The dry powder inhaler according to claim 1, characterized in that the dry powder inhaler (1) is designed such that the carrier (5) is capable of being moved or indexed stepwise from one of said multiple storage members (6) to the next one of said multiple storage members (6).

11. The dry powder inhaler according to claim 1, characterized in that the multiple storage members (6) or nozzles (11) are sealed by one common sealing or cover layer (8).

12. The dry powder inhaler of claim 1, wherein the storage device (4) or carrier (5) is a peelable blister strip, wherein the nozzle (11) is capable of being opened one after the other by peeling the blister strip.

13. The dry powder inhaler of claim 1, wherein the carrier (5) carries the storage members (6) formed separately from the carrier (5) rigidly or in a unmovable manner and is adapted that each of the storage members (6) or the nozzle (11) is capable of being opened without movement of the storage members (6) or a base layer (7) thereof by opening or peeling a common sealing or cover layer (8).

14. The dry powder inhaler of claim 1, further comprising a mouthpiece including a longitudinal body having an inlet end and an outlet end, the inlet end being in fluid communication with the outlet of the respective nozzle (11), and the outlet end for delivering the dose of the medical powder formulation (2) to a user, wherein the outlet of the nozzle (11), the inlet end of the longitudinal body, and the outlet end of the longitudinal body are oriented along the dispensing direction (12).

15. The dry powder inhaler of claim 1, wherein the duct (10) is always open and remains open even prior to dispensing of the powder formulation.

16. A storage device (4) for a medical powder formulation (2) containing a drug, for a dry powder inhaler (1), the storage device (4) comprising:

a carrier (5) having multiple storage members (6) in a flexible, band-like arrangement, wherein each of said multiple storage members (6) includes: (i) a respective storage cavity (9) containing a dose of the medical powder formulation (2), and (ii) a respective nozzle (11) having an outlet oriented such that the respective medical powder formulation dose (2) is dispensed from the respective storage cavity (9), through the respective nozzle, and outward from the outlet in a dispensing direction (12), characterized in that the respective nozzle (11) includes a duct (10) that forms a channel from the storage cavity (9) to the outlet, where the duct (10) is formed integrally with the storage cavity (9), and the dispensing direction (12) of the respective nozzle (11) is directed in a lengthwise direction of the carrier (5).

17. A method, comprising:

dispensing a medical powder formulation (2) containing a drug, as a dry powder spray (3) from a blister strip comprising multiple storage members (6), wherein each of said multiple storage members (6) includes (i) a respective storage cavity (9) containing a dose of the medical powder formulation (2), and (ii) a respective nozzle (11) having an outlet oriented such that the medical powder formulation dose (2) is dispensed from the respective storage cavity (9), through the respective nozzle, and outward from the outlet in a dispensing direction (12), wherein the respective nozzle (11) includes a duct (10) that forms a channel from the storage cavity (9) to the outlet, where the duct (10) is formed integrally with the storage cavity (9), and the dispensing direction (12) of the respective nozzle (11) is directed in a lengthwise direction of the carrier (5), and peeling the blister strip to open each of the multiple storage members (6) and expose the respective nozzle (11), one after the other, so that the medical powder formulation dose (2) in each of said multiple storage members (6) is dispensed one after the other.

18. Method according to claim 17, characterized in that each of the storage members (6) or nozzle (11) is sealed by one common sealing or cover layer (8), wherein the common sealing or cover layer (8) is peeled.

19. Method according to claim 17, characterized in that the storage members (6) are individually connected to a supply of pressurized gas by piercing each of the respective storage members (6) by means of a piercing element (15).

\* \* \* \* \*